(12) United States Patent
Porat et al.

(10) Patent No.: US 8,158,412 B2
(45) Date of Patent: Apr. 17, 2012

(54) INOCULATION LOOP ASSEMBLY

(75) Inventors: Gadi Porat, Jerusalem (IL); Joel Stern, Herzliya (IL); Yoram Cohen, Shoham (IL)

(73) Assignee: Associates for Public Health, Jerusalem (IL)

( * ) Notice: Subject to any disclaimer, the term of this patent is extended or adjusted under 35 U.S.C. 154(b) by 675 days.

(21) Appl. No.: 12/373,321

(22) PCT Filed: Jul. 12, 2007

(86) PCT No.: PCT/IL2007/000877
§ 371 (c)(1),
(2), (4) Date: Jan. 12, 2009

(87) PCT Pub. No.: WO2008/007376
PCT Pub. Date: Jan. 17, 2008

(65) Prior Publication Data
US 2009/0286310 A1    Nov. 19, 2009

Related U.S. Application Data

(60) Provisional application No. 60/830,327, filed on Jul. 13, 2006.

(51) Int. Cl.
*C12M 3/00* (2006.01)
*C12M 1/26* (2006.01)
*C12M 1/00* (2006.01)

(52) U.S. Cl. ............... 435/309.3; 435/308.1; 435/307.1; 435/309.2; 435/309.1; 422/500; 422/501; 422/568

(58) Field of Classification Search ............... 435/309.3, 435/308.1, 307.1, 309.2, 309.1; 422/500, 422/501, 568
See application file for complete search history.

(56) References Cited

U.S. PATENT DOCUMENTS
3,796,638 A    3/1974 Guigan
(Continued)

OTHER PUBLICATIONS
International Search Report for PCT/IL07/00877 filed Jul. 12, 2007.
(Continued)

*Primary Examiner* — Nathan Bowers
(74) *Attorney, Agent, or Firm* — Paul D. Bianco; Fleit Gibbons Gutman Bongini & Bianco PL

(57) ABSTRACT

A disposable inoculation loop assembly comprising a test tube and a tube stopper adapted to fit into a free end of the test tube. A first end of the stopper faces into the interior of the test tube substantially hermetically sealing the interior of the test tube. The assembly further includes an inoculation loop fixed to the tube stopper and extending into the interior of the test tube to a predetermined distance when the stopper is positioned in the free end of the test tube. The assembly when assembled is sterilized and pre-evacuated to a predetermined vacuum which is sufficient to draw a volume of a bodily liquid to be sampled into the test tube. The volume is of such an amount so that the liquid level in the test tube substantially just covers a predetermined portion of the inoculation loop.

6 Claims, 2 Drawing Sheets

U.S. PATENT DOCUMENTS

| | | | |
|---|---|---|---|
| 3,844,895 A * | 10/1974 | Rose et al. | ........... 435/297.2 |
| 4,116,066 A | 9/1978 | Mehl et al. | |
| 4,300,404 A | 11/1981 | Mehl et al. | |
| 4,687,746 A | 8/1987 | Rosenberg | |
| 4,892,831 A | 1/1990 | Wong | |
| 4,927,605 A | 5/1990 | Dorn | |
| 5,279,964 A | 1/1994 | Chrisope | |
| 5,330,899 A | 7/1994 | DeVaughn | |
| 5,616,499 A | 4/1997 | Eckner | |
| 6,921,395 B2 | 7/2005 | Carano | |
| 2003/0129738 A1 * | 7/2003 | Sorenson et al. | ........... 435/287.1 |
| 2004/0151634 A1 | 8/2004 | Anderson | |

OTHER PUBLICATIONS

Written Opinion published for PCT/IL07/00877 filed Jul. 12, 2007.

* cited by examiner

INOCULATION LOOP ASSEMBLY

FIELD OF THE INVENTION

The present invention relates to an inoculation loop assembly for use in culturing microorganisms.

BACKGROUND OF THE INVENTION

Disposable, plastic inoculation loops for culturing microorganisms are known in the art. These are often formed of moldable synthetic resins, such as polystyrene or polypropylene. These inoculation loops are generally shaped as a rod having a loop eye formed on one of the rod's ends and are used for streaking culture media employed in culturing microbes. Culturing may be carried out using any of many different types of bodily fluids. These include, but are not limited to, urine, blood, saliva, etc.

When culturing a sample of a bodily fluid, the volume of fluid transferred from the sample collection vessel to the culture medium (or media) must be known with reasonable accuracy. Accordingly, when using an inoculation loop, the end with the loop eye must be immersed in the fluid sample up to a pre-determined level. Generally, when dipping the loop eye into the liquid too far or not far enough, an incorrect volume of liquid is transferred to the culturing medium. The number of colony forming units (cfu) found in microbial cultures is a quantitative measure predicting infection. Since the cfu count is directly dependent on the volume of sample used, false positives and false negatives often result when incorrect volumes are used.

The whole culturing process must be kept free from contamination. Contamination can occur in the sample collection vessel itself since the vessel is usually uncovered for at least a short period of time. It may also occur during the transfer of sample to be cultured via the inoculation loop to a Petri dish filled with a culture medium. During the transfer, the inoculation device may be exposed to air-borne microorganisms, and the longer the exposure, the greater the likelihood of contamination. After using the inoculation loop to streak the culture medium with the sample, the medium is incubated for a prescribed period.

Normal culturing uses an inoculation loop to transfer a sample to be cultured from a sample collection vessel to a growth medium (media) in a Petri dish. Typical inoculation loops and their use are described in U.S. Pat. Nos. 4,892,831 to Wong; 4,687,746 to Rosenberg et al; and 5,279,964 to Chrisope, all of which are incorporated by reference herein.

Recently, other types of devices for microbial culturing of urine, e.g. the dipslides of Oxoid Ltd. of Basingstoke UK or Orion Diagnostica Oy of Espoo Finland, and the DipStreak of Novamed Ltd. of Jerusalem Israel, have been developed. These devices are plastic plates, each side of which is coated with a different culture medium. The dipslide is totally immersed in the bodily fluid. The DipStreak has projections which are carefully and partially immersed in the bodily fluid. The projections are then detached and used to streak both sides of the culture media coated plate. Both dipslides and the DipStreak devices still suffer from the disadvantages noted above. They are susceptible to sample contamination and quantitative analysis of the sample is susceptible to false readings. In addition, these devices are generally more costly then inoculation loops used in conjunction with culture medium filled Petri dishes. Sample contamination occurs inter alia because the collection vessel is typically an open vessel. Additionally, these devices are not stable and require two handed use, one hand holding the collection vessel and the other holding the dipslide or DipStreak.

In view of the above, it would be advantageous to develop an inoculation system for bacteriological or microbial culturing of bodily fluids which reduces the dangers of contamination. Additionally, it would be advantageous to develop a system wherein the culturing of microbes in body fluids would not require extremely careful immersion of an inoculation loop in the fluid sample. With less care required, persons not necessarily trained in microbiological procedures can use the system. There is a need for an inoculation system which will reduce the false positive and false negative results when culturing microbes. It would also be advantageous to develop a system that is disposable and of low cost.

SUMMARY OF THE PRESENT INVENTION

It is an object of the present invention to provide an inoculation loop assembly which reduces opportunities for contamination of microbial cultures.

It is also an object of the present invention to provide an inoculation loop assembly which is simpler to use and provides more consistently accurate results, reducing the rate of false positives and negatives.

It is a further object of the present invention to provide a low cost inoculation loop assembly for use in microbial culturing which requires less attention and training on the part of the person carrying out the procedures.

It is a further object of the invention to provide an inoculation loop assembly for use at the point of sample collection and not just in the laboratory in which culture incubation usually takes place.

There is thus provided in accordance with one aspect of the present invention a disposable inoculation loop assembly. The assembly comprises a test tube and a tube stopper having first and second ends. The stopper is adapted to fit into a free end of the test tube such that the first end faces into the interior of the test tube and substantially hermetically seals the interior of the test tube from the ambient. The assembly further includes an inoculation loop fixed to the tube stopper so that it extends into the interior of the test tube to a predetermined distance when the stopper is positioned in the free end of the test tube. The assembly when assembled is sterilized and pre-evacuated to a predetermined vacuum sufficient to draw a volume of a bodily liquid to be sampled into the test tube. The volume being drawn is of an amount such that the liquid level in the test tube substantially just covers a predetermined portion of the inoculation loop.

In one embodiment of the assembly, the stopper has a predetermined cannula insertion location through which a liquid sampling cannula is inserted, thereby facilitating the delivery of a liquid sample to the test tube. In some instances of this embodiment, the inoculation loop is fixed to the stopper at a location which is not in registration with the cannula insertion location. The sample liquid enters the test tube via a sharpened end of the cannula and is delivered into the test tube without impinging upon the inoculation loop. In other instances of this embodiment, a portion of the inoculation loop has a liquid conducting portion, bounded by a liquid inlet and by a liquid outlet. The outlet is formed so as to face generally outwards toward an adjacent test tube wall portion. The predetermined cannula insertion location is positioned in registration with the liquid inlet. This allows liquid to be dispensed from the cannula into the liquid inlet after which the liquid flows along the liquid conducting portion so as to be delivered into the test tube via the liquid outlet. Delivery of the liquid via the liquid outlet is effected so as not to impinge upon the inoculation loop. In this last instance of the present embodiment, the inoculation loop and the cannula insertion location may be both positioned centrically with respect to the stopper.

In yet another embodiment of the assembly, the inoculation loop comprises a rod and a loop eye positioned at one end of the rod. The volume of the bodily liquid being drawn is in an amount such that the liquid level in the test tube substantially just covers the loop eye. In some instances of this embodiment, the stopper has a predetermined cannula insertion location through which a liquid sampling cannula is inserted, thereby facilitating the delivery of a liquid sample to the test tube. In some instances, the inoculation loop is fixed to the stopper at a location which is not in registration with the cannula insertion location, such that sample liquid entering the test tube via a sharpened end of a cannula is delivered into the test tube without impinging upon the inoculation loop. In yet other instances, a portion of the inoculation loop has a liquid conducting portion bounded by a liquid inlet and by a liquid outlet, the outlet formed so as to face generally outwards toward an adjacent test tube wall portion. The predetermined cannula insertion location is positioned in registration with the liquid inlet, such that liquid is dispensed from the cannula into the liquid inlet, whereafter the liquid flows along the liquid conducting portion so as to be delivered into the test tube via the liquid outlet. When delivered via the liquid outlet the liquid does not impinge upon the inoculation loop.

In yet another aspect of the present invention there is provided a disposable inoculation loop kit. The kit comprises an inoculation loop assembly, a sample collection vessel for collecting a liquid sample of a bodily fluid, and a cannula having at least one sharpened end for piercing the stopper noted below and for transferring sample liquid from a vessel to a test tube of the assembly. The transfer is effected by the predetermined vacuum in the test tube. The assembly comprises a test tube and a tube stopper having first and second ends. The stopper is adapted to fit into a free end of the test tube such that the first end faces into the interior of the test tube and substantially hermetically seals the interior of the test tube from the ambient. The assembly further includes an inoculation loop fixed to the tube stopper so that it extends into the interior of the test tube to a predetermined distance when the stopper is positioned in the free end of the test tube. The assembly when assembled is sterilized and pre-evacuated to a predetermined vacuum sufficient to draw a volume of a bodily liquid to be sampled into the test tube. The volume being drawn is of an amount such that the liquid level in the test tube substantially just covers a predetermined portion of the inoculation loop.

In one embodiment of the kit, the inoculation loop comprises a rod and a loop eye positioned at one end of the rod. The volume of the bodily liquid being drawn is in an amount such that the liquid level in the test tube substantially just covers the loop eye. In some instances of this embodiment, the stopper has a predetermined cannula insertion location through which the liquid sampling cannula is inserted, thereby facilitating the delivery of a liquid sample to the test tube. In some of these instances, the inoculation loop is fixed to the stopper at a location which is not in registration with the cannula insertion location, such that sample liquid entering the test tube via a sharpened end of the cannula is delivered into the test tube without impinging upon the inoculation loop. In yet other instances, a portion of the inoculation loop has a liquid conducting portion bounded by a liquid inlet and by a liquid outlet, the outlet formed so as to face generally outwards toward an adjacent test tube wall portion. The predetermined cannula insertion location is positioned in registration with the liquid inlet, such that liquid is dispensed from the cannula into the liquid inlet, whereafter the liquid flows along the liquid conducting portion so as to be delivered into the test tube via the liquid outlet. When delivered via the liquid outlet, the liquid does not impinge upon the inoculation loop.

In another embodiment of the kit, the stopper has a predetermined cannula insertion location through which the liquid sampling cannula is inserted, thereby facilitating the delivery of a liquid sample to the test tube. In some instances of this embodiment, the inoculation loop is fixed to the stopper at a location which is not in registration with the cannula insertion location. The sample liquid enters the test tube via a sharpened end of the cannula and is delivered into the test tube without impinging upon the inoculation loop. In other instances of this embodiment, a portion of the inoculation loop has a liquid conducting portion bounded by a liquid inlet and by a liquid outlet. The outlet is formed so as to face generally outwards toward an adjacent test tube wall portion. The predetermined cannula insertion location is positioned in registration with the liquid inlet. This allows liquid to be dispensed from the cannula into the liquid inlet, after which the liquid flows along the liquid conducting portion so as to be delivered into the test tube via the liquid outlet. Delivery of the liquid via the liquid outlet is effected so as not to impinge upon the inoculation loop. In this last instance of this embodiment, the inoculation loop and the cannula insertion location may both be positioned centrically with respect to the stopper.

DEFINITIONS

Proximal—the direction closest to the stopper of the test tube.

Distal—the direction furthest from the stopper of the test tube.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in greater detail than is necessary for a fundamental understanding of the invention. The description taken with the drawings make apparent to those skilled in the art how the several forms of the invention may be embodied in practice.

In the drawings.

Similar elements in the Figures are numbered with similar reference numerals.

DESCRIPTION OF PREFERRED EMBODIMENTS

Figure 1:
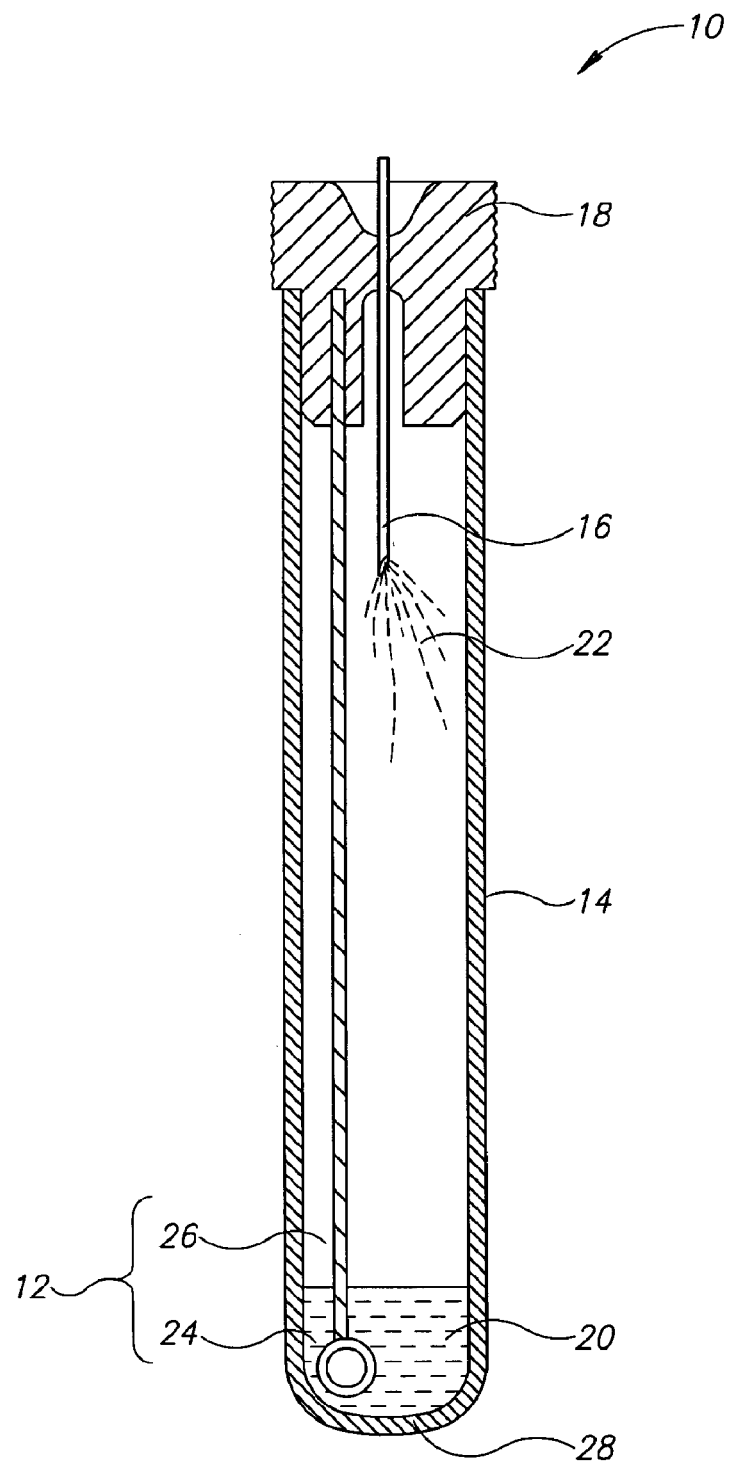
FIG. 1 is a side view of a disposable inoculation loop assembly constructed according to an embodiment of the present invention.

Currently, bacteriological or other microbial culturing of urine samples are usually carried out with an inoculation loop consisting of a rod and having a loop, denoted herein as an inoculation loop eye or a loop eye, positioned at one end of the rod. The inoculation loop eye is carefully dipped in a specimen cup containing collected urine. The depth of the dip has well-defined limits and the technician preparing the culture must work very carefully. In general, the inoculation loop must be dipped into the urine specimen so that the loop eye is completely covered allowing it to pick up a known volume of liquid. Additional liquid which can adhere to the rod of the inoculation loop above the loop eye is to be avoided. If a portion of the inoculation loop's rod enters the specimen, an amount of liquid greater than that required will be applied to the culture medium. Since the number of colony forming units upon which diagnosis is based is directly related to the sample volume deposited on the culture medium, any excess or shortage of volume can generate a false positive or false negative result, respectively.

While the inoculation loop is manufactured under sterile conditions it must be used under non-sterile conditions. The specimen collection cup is often open to the environment and the inoculation loop must transfer the sample to be cultured, typically in an amount of 1 or 10 microliters, in an open air environment where airborne microorganisms are present.

The present invention teaches a disposable sterile inoculation loop assembly wherein a plastic inoculation loop is implanted, that is fixed, in a stopper. The stopper snugly fits into the mouth of a test tube. The covered test tube is prepared so that it is under a predetermined vacuum. When the entire assembly is assembled it is irradiated to effect sterilization. The vulnerability of the inoculation loop assembly to contamination is reduced since the test tube is opened only immediately preceding streaking of the culture with the inoculation loop. Additionally, the pre-determined, pre-calibrated vacuum allows drawing off of a liquid sample from the sample collection cup which is substantially that amount of sample required to just cover the inoculation loop eye. In that way neither an excess nor a shortage of sample will be streaked onto the growth medium used for culturing.

While what is described herein is described with regard to bacteriological or other microbial culturing of urine samples, typically carried out to diagnosis urinary tract infections (UTIs), it should be evident to one skilled in the art that the inoculation loop assembly of the present invention may be used with other bodily fluids such as blood, and saliva. It should also be understood that the assembly of the present invention may be used with liquids other than bodily liquids. Wherever the culturing of microorganisms is required, such as with liquid food stuffs, water supply systems or liquid waste deposits, the assembly of the present invention may be used. In what is described herein whenever the term "culture medium" is used, it should be understood that a plurality of media may also be used and not necessarily a single medium.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Reference is now made to FIG. 1 which shows a side view of a disposable inoculation loop assembly for use in bacteriological or other microbial culturing of bodily fluids. As noted above, the discussion will refer to urine testing. However, it should be evident to one skilled in the art that the assembly of the present invention may also be used for microbiological testing of other bodily fluids, such as blood, saliva, etc. Similarly, bacteriological or other microbial culturing of biological fluids of species other than humans may also make use of the inoculation loop assembly described herein.

FIG. 1 shows inoculation loop assembly 10 which includes a test tube 14, a tube stopper 18, and a plastic disposable inoculation loop 12 fixed in, and supported by, tube stopper 18. All elements have been sterilized, typically, but without being limiting, by using gamma radiation. Inoculation loop 12 includes a loop eye 24 connected to a rod 26 and is formed of any of many plastics well known in the art, such as polystyrene. Inoculation loop 12 is embedded, that is implanted or fixed, in tube stopper 18 prior to closing inoculation assembly 10. Loop eye 24 of inoculation loop 12 may be constructed so as to be sized to transfer any desired volume of sample. Typically, the loop eyes are sized to transfer 1 or 10 microliter samples. Inoculation loop 12 is generally imbedded, that is fixed, in stopper 18 eccentrically so as not to interfere with the inflow of sample drawn off from a sample collection vessel as will be described below.

Tube stopper 18 is constructed of flexible, liquid impermeable, pierceable material that preferably may be self-sealing to liquids after being pierced. The material from which stopper 18 may be formed includes, but is not limited to, moldable rubbers, polymeric resins, and silicones. The exact shape of the stopper is easily producible by any of many techniques known in the art, such as, but without intending to be limiting, by injection molding.

Vacutainers® manufactured by Becton Dickinson & Co. of Franklin Lakes, N.J. may be used as a source of test tubes 14. Suitable inoculating loops made of plastic or other disposable material can be obtained from, for example, Cole Palmer Instrument Company of Vernon Hills, Ill. or Fisher Scientific of Suwanee, Ga. Test tubes 14 may be made of any of many plastics known in the art, such as polystyrene (PS) and polyethylene terephtalate (PET), or of glass.

Cannula 16, shown in FIG. 1, is actually attached to, and part of, a closed urine collection cup (not shown). Cannula 16 can be used to pierce stopper 18 and transfer a predetermined volume of sample from the collection cup to partially evacuated test tube 14. Collection cups with cannula are known in the art and sold commercially for example by Becton Dickinson and Co. of Franklin Lakes, N.J.

Test tube 14 with stopper 18 and with inoculation loop 12 embedded therein is prepared so as to be under a pre-selected vacuum. The pre-selected vacuum is empirically determined and is intended to draw off a pre-determined volume of sample from the urine sample collection cup (not shown) through cannula 16. The pre-selected vacuum, and therefore the pre-selected sample volume to be drawn off, is intended to just cover loop eye 24 of inoculation loop 12. As noted previously, sample volume is critical with false positives and negatives resulting from providing a larger or smaller volume than is required for culturing.

The predetermined vacuum obviates the need for the technician to exercise exceptional care when dipping loop eye 24 into liquid 20 in order to preclude an excess or a shortfall of sample liquid being taken for culturing. The pre-selection and pre-calibration of the vacuum can be effected for any size loop eye. Commercially available inoculation loops with loop eyes of 1 microliter and 10 microliter can be pre-calibrated.

It is expected that a vacuum of 1-3 inches of Hg (approximately 25-76 Torr or about 0.033-0.100 bar) in a 10 ml tube will be sufficient to draw about 1 ml of sample into the pre-evacuated test tube 14 which forms part of inoculation loop assembly 10. This is expected to be sufficient to just cover loop eye 24 of inoculation loop 12.

Becton-Dickenson's 10 ml Vacutainers® are typically produced so as to have a vacuum of about 19-20 inches Hg (about 500 Torr or about 0.66 bar) when about 9 ml of urine is to be drawn from a urine collection cup. But such volumes are far in excess of what is required when "automatic" dipping of loop eye 24 is desired, as it is in the present invention.

Cannula 16 in FIG. 1, when piercing and inserted into and through stopper 18, is positioned eccentrically so that the liquid drawn off from the sample collection vessel (not shown) does not touch, and possibly remain on, rod 26 of inoculation loop 12. The drawn off liquid 20 drops substantially straight down to the floor 28 of test tube 14.

Additionally, because inoculation loop 12 is not exposed to the air after sterilization until immediately before loop eye 24 is used to streak a culture medium filled Petri dish, air borne microorganisms only minimally, if at all, contaminate the specimens.

Figures 2A, 2B, 2C:
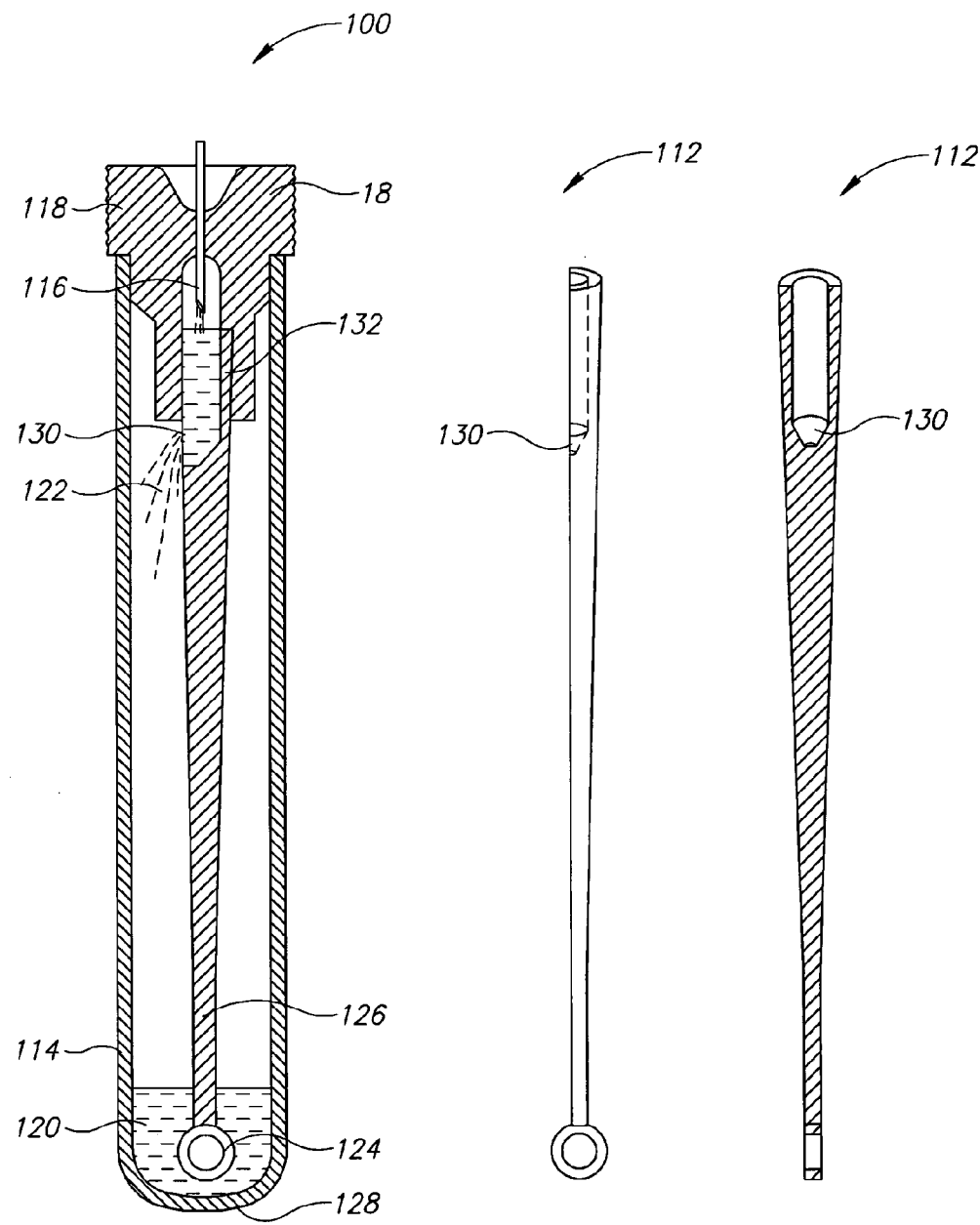
FIG. 2A is a side view of a disposable inoculation loop assembly constructed according to a second embodiment of the present invention.
FIGS. 2B and 2C are two additional views of the disposable inoculation loop used in the inoculation loop assembly shown in FIG. 2A.

Reference is now made to FIGS. 2A-2C where a second embodiment of the present assembly is shown. The second embodiment is very similar to the first and similar elements are given identical numbering but with the addition of a prefix digit, 1. Accordingly, a description of the elements will not be repeated as their structure and operation are similar to the first embodiment. It should be noted that in this second embodiment, cannula 116 is positioned in the center of tube stopper 118.

FIGS. 2A-2C show that cannula 116 and inoculation loop 112 are centrically positioned in stopper 118; cannula 116 is also collinearly positioned with inoculation loop 112. Inoculation loop 112 is at least partially hollow at its proximal end 132 and drawn off liquid enters this hollow from cannula 116. It also has an aperture 130 in its side wall through which the bodily fluid exits from the hollow into test tube 114. Aperture 130 allows the sample liquid to exit through the side of inoculation loop 112 and substantially along the walls of test tube 114. In this way, liquid builds up at the bottom 128 of test tube 114 without necessarily touching, and thereby adhering to, rod 126 of inoculation loop 112. This liquid build up is again controlled by the existence of a pre-determined vacuum which allows liquid to build up substantially only until it reaches the top of loop eye 124.

Inoculation assemblies 10 (FIG. 1) and 110 (FIG. 2A-2C), with their pre-calibrated vacuums, draw off sample liquid in a manner similar to that shown and discussed in U.S. Pat. Nos. 6,921,395 to Carano et al; 4,927,605 to Dorn et al; 4,116,066 to Mehl et al; and 4,300,404 to Mehl et al, all herein incorporated by reference. In these patents, an evacuated test tube is mated with a sample collection vessel. Sample liquid moves under vacuum from the collection vessel to the test tube via a needle cannula which pierces a stopper of the test tube. The covered sample collection vessel typically possesses a recess in its cover which contains the cannula used in the liquid transfer. The recess functions as a female structure to receive the evacuated test tube, the male structure, during sample transfer.

Because the inoculation loop of the present invention is removed for only a short period of time from the sterilized test tube and then only when proximate to the culture medium to be streaked, possible microbial contamination is minimized. Additionally, because the fluid is pulled off by vacuum directly from a closed sample collection vessel to a closed test tube, the risk of infection to the medical staff is reduced.

Because the inoculation loop assembly of the present invention includes a loop intended for streaking culture medium filled Petri dishes, costs are lower than when dipslides and Novamed's DipStreak plates are used.

The present invention also teaches a disposable inoculation loop kit. The kit comprises an inoculation loop assembly as described above, a sample collection vessel for collecting a biological fluid, and a cannula for transferring a portion of the biological fluid collected in the collection vessel to the pre-evacuated test tube of the assembly.

While the invention has been described in terms of inoculation loops, it is contemplated that the invention is also applicable, with little or no modification, to conventional inoculation needles used in microbial culturing procedures. Therefore, wherever the term "inoculation loop" is used it is to be viewed as including inoculation needles.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. Therefore, it will be appreciated by persons skilled in the art that the present invention is not limited by what has been particularly shown and described herein above. Rather the scope of the invention is defined by the claims that follow.

What is claimed is:

1. A disposable inoculation loop assembly comprising:
   a test tube;
   a tube stopper having first and second ends and adapted to fit into a free end of said test tube such that said first end faces into the interior of said test tube, and so as to substantially hermetically seal the interior of said test tube from the ambient, said stopper having a predetermined cannula insertion location for the insertion therethrough of a liquid sampling cannula; and
   an inoculation loop fixed to said tube stopper so as to extend into the interior of said test tube to a predetermined distance when said tube stopper is positioned in said free end of said test tube,
   wherein a portion of said inoculation loop has a liquid conducting portion, bounded by a liquid inlet, and by a liquid outlet, said outlet formed so as to face generally outwards toward an adjacent test tube wall portion, and wherein said predetermined cannula insertion location is positioned in registration with said liquid inlet, such that liquid is dispensed from the cannula into said liquid inlet, whereafter the liquid flows along said liquid conducting portion so as to be delivered into said test tube via said liquid outlet so as not to impinge upon said inoculation loop, and wherein said assembly when assembled is sterilized and pre-evacuated to a predetermined vacuum sufficient to draw a volume of a bodily liquid to be sampled into said test tube, said volume being of such an amount so that the liquid level in said test tube substantially just covers a predetermined portion of said inoculation loop.

2. A disposable inoculation loop assembly according to claim 1 wherein said inoculation loop and said cannula insertion location are both positioned centrically with respect to said stopper.

3. A disposable inoculation loop assembly according to claim 1, wherein said inoculation loop comprises a rod and a loop eye positioned at one end of said rod, the volume of the bodily liquid being drawn is in an amount so that the liquid level in said test tube is such that it substantially just covers said loop eye.

4. A disposable inoculation loop kit comprising:
an inoculation loop assembly comprising:
   a test tube;
   a tube stopper having first and second ends and adapted to fit into a free end of said test tube such that said first end faces into the interior of said test tube, and so as to substantially hermetically seal the interior of said test tube from the ambient, said stopper having a predetermined cannula insertion location for the insertion therethrough of said liquid sampling cannula; and
   an inoculation loop fixed to said tube stopper so as to extend into the interior of said test tube to a predetermined distance when said tube stopper is positioned in said free end of said test tube,
   wherein a portion of said inoculation loop has a liquid conducting portion, bounded by a liquid inlet, and by a liquid outlet, said outlet formed so as to face generally outwards toward an adjacent test tube wall portion, and wherein said predetermined cannula insertion location is positioned in registration with said liquid inlet, such that liquid is dispensed from the cannula into said liquid inlet, whereafter the liquid flows along said liquid conducting portion so as to be delivered into said test tube via said liquid outlet so as not to impinge upon said inoculation loop, and
   wherein said assembly when assembled is sterilized and pre-evacuated to a predetermined vacuum sufficient to draw a volume of a bodily liquid to be sampled into said test tube, said volume being of such an amount so that the liquid level in said test tube substantially just covers a predetermined portion of said inoculation loop; and
a sample collection vessel for collecting a liquid sample of a bodily fluid; and
a cannula having at least one sharpened end for piercing said stopper and transferring sample liquid from said vessel to said test tube of said assembly, the transfer effected by the predetermined vacuum in said test tube.

5. A disposable inoculation loop kit according to claim 4, wherein said inoculation loop and said cannula insertion location are both positioned centrically with respect to said stopper.

6. A disposable inoculation loop kit according to claim 4, wherein said inoculation loop comprises a rod and a loop eye positioned at one end of said rod, the volume of the bodily liquid being drawn is in an amount so that the liquid level in said test tube is such that it substantially just covers said loop eye.

* * * * *

UNITED STATES PATENT AND TRADEMARK OFFICE
CERTIFICATE OF CORRECTION

PATENT NO. : 8,158,412 B2
APPLICATION NO. : 12/373321
DATED : April 17, 2012
INVENTOR(S) : Gadi Porat et al.

It is certified that error appears in the above-identified patent and that said Letters Patent is hereby corrected as shown below:

Title Page, Item (73) Assignee:
Change "Associates" for Public Health to --Association-- for Public Health Signed and Sealed this
Twenty-eighth Day of August, 2012

David J. Kappos
*Director of the United States Patent and Trademark Office*